US00PP34492P2

(12) United States Plant Patent
Ullrich

(10) Patent No.: US PP34,492 P2
(45) Date of Patent: Aug. 16, 2022

(54) ROSE PLANT NAMED 'ESM R432'

(50) Latin Name: *Rosa hybrida*
Varietal Denomination: ESM R432

(71) Applicant: TECNOVIV LLC, Miami, FL (US)

(72) Inventor: Clarisse Ullrich, Quito (EC)

(73) Assignee: TECNOVIV LLC, Miami, FL (US)

( * ) Notice: Subject to any disclaimer, the term of this patent is extended or adjusted under 35 U.S.C. 154(b) by 0 days.

(21) Appl. No.: 17/669,101

(22) Filed: Feb. 10, 2022

(51) Int. Cl.
*A01H 5/02* (2018.01)
*A01H 6/74* (2018.01)

(52) U.S. Cl.
USPC ..... Plt./149

(58) Field of Classification Search
USPC ..... Plt./101, 141, 149
See application file for complete search history.

*Primary Examiner* — Karen M Redden
(74) *Attorney, Agent, or Firm* — C. Anne Whealy

(57) ABSTRACT

A new and distinct cultivar of Rose plant named 'ESM R432', characterized by its upright and strong flowering stems; vigorous growth habit; dark green-colored leaves; dark pink-colored flowers; and excellent postproduction longevity.

1 Drawing Sheet

Botanical designation: *Rosa hybrida.*
Cultivar denomination: 'ESM R432'.

STATEMENT REGARDING PRIOR DISCLOSURES BY INVENTOR AND APPLICANT/ASSIGNEE

An European Community Plant Breeder's Rights application for the instant plant was filed by the Applicant/Assignee of the instant application, Tecnoviv LLC of Miami, Fla. on Jun. 27, 2019, application number 2019/1595. Foreign priority is not claimed to this European Community Plant Breeder's Rights application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present Invention relates to a new and distinct cultivar of Rose plant, botanically known as *Rosa hybrida*, commercially used as a cut flower Rose plant, and hereinafter referred to by the name 'ESM R432'.

The new Rose plant is a product of a planned breeding program conducted by the Inventor in El Quinche, Pichincha, Ecuador. The objective of the breeding program was to develop new cut flower Rose varieties with attractive flowers and excellent postproduction longevity.

The new Rose plant originated from a cross-pollination made by the Inventor in August, 2013 of a proprietary Rose selection identified as Line R795, not patented, as the female, or seed, parent with a proprietary Rose selection identified as Line R338, not patented, as the male, or pollen, parent. The new Rose plant was discovered and selected by the Inventor as a single flowering plant within the progeny of the stated cross-pollination in a controlled greenhouse environment in El Quinche, Pichincha, Ecuador in February, 2015.

Asexual reproduction of the new Rose plant by bud grafting in El Quinche, Pichincha, Ecuador since December, 2015 has shown that the unique features of this new Rose plant are stable and reproduced true to type in successive generations of asexual reproduction.

SUMMARY OF THE INVENTION

Plants of the new Rose have not been observed under all possible combinations of environmental conditions and cultural practices. The phenotype may vary somewhat with variations in environmental conditions such as temperature and light intensity, without however, any variance in genotype.

The following traits have been repeatedly observed and are determined to be the unique characteristics of 'ESM R432'. These characteristics in combination distinguish 'ESM R432' as a new and distinct Rose plant:

1. Upright and strong flowering stems.
2. Vigorous growth habit.
3. Dark green-colored leaves.
4. Dark pink-colored flowers.
5. Excellent postproduction longevity.

Plants of the new Rose differ from plants of the female parent selection in the following characteristics:

1. Plants of the new Rose are slightly less vigorous than plants of the female parent selection.
2. Stems of plants of the new Rose are longer than stems of plants of the female parent selection.
3. Flowers of plants of the new Rose are not as fragrant as flowers of plants of the female parent selection.
4. Plants of the new Rose have dark pink-colored flowers whereas plants of the female parent selection have lavender-colored flowers.

Plants of the new Rose differ from plants of the male parent selection in the following characteristics:

1. Plants of the new Rose are more vigorous than plants of the male parent selection.
2. Flowers of plants of the new Rose are more fragrant than flowers of plants of the male parent selection.
3. Plants of the new Rose have dark pink-colored flowers whereas plants of the male parent selection have cream-colored flowers.

Plants of the new Rose can also be compared to plants of *Rosa hybrida* 'Sweetness', not patented. In side-by-side comparisons, plants of the new Rose differ from plants of 'Sweetness' in the following characteristics:

1. Plants of the new Rose are taller than plants of 'Sweetness'.
2. Stems of plants of the new Rose have fewer thorns than stems of plants of 'Sweetness'.
3. Plants of the new Rose have larger flowers than plants of 'Sweetness'.

BRIEF DESCRIPTION OF THE PHOTOGRAPH

The accompanying colored photographic sheet illustrates the overall appearance of the new Rose plant showing the colors as true as it is reasonably possible to obtain in colored reproductions of this type. Colors in the photograph may differ slightly from the color values cited in the detailed botanical description which accurately describe the colors of the new Rose plant.

On the left side of the photographic sheet is a side perspective view of a typical flowering stem of 'ESM R432'.

At the upper right of the photographic sheet is a close-up view of a typical developed flower of 'ESM R432'.

And at the lower right of the photographic sheet are close-up views of the upper and lower surfaces of typical leaves of 'ESM R432'.

DETAILED BOTANICAL DESCRIPTION

The aforementioned photographs, following observations and measurements describe plants grown in ground beds in a polyethylene-covered greenhouse in Cayambe, Pichincha, Ecuador and under typical cut Rose production practices. Plants were pinched 14 weeks after planting and were 21 months old when the photograph and the description were taken. During the production of the plants, day temperatures ranged from 17° C. to 21° C., night temperatures ranged from 5° C. to 8° C. and light levels averaged 19,338 lux. In the following description, color references are made to The Royal Horticultural Society Colour Chart, 2015 Edition, except where general terms of ordinary dictionary significance are used.

Botanical classification: *Rosa hybrida* 'ESM R432'.

Parentage:

*Female, or seed, parent*.—Proprietary seedling selection of *Rosa hybrida* identified Line R795, not patented.

*Male, or pollen, parent*.—Proprietary seedling selection of *Rosa hybrida* identified Line R338, not patented.

Propagation:

*Type*.—By bud grafting.

*Time to initiate roots, summer*.—About 15 days at temperatures about 26° C. to 30° C.

*Time to produce a rooted young plant, summer*.—About 30 days at temperatures about 22° C. to 26° C.

*Root description*.—Medium in thickness, fibrous; typically greyish brown in color, actual color of the roots is dependent on substrate composition, water quality, fertilizers, substrate temperature and age of roots.

*Rooting habit*.—Moderately freely branching; dense.

Plant description:

*Plant and growth habit*.—Perennial shrub; upright and strong flowering stems; typically grown as a standard type; vigorous growth habit and rapid growth rate.

*Productivity*.—Plants of the new Rose are highly productive with about 84.5 flowering stems developing per $m^2$ per year.

*Plant height*.—About 189.5 cm.

*Plant width* (*spread*).—About 53 cm.

*Lateral branches*.—Length: About 141.8 cm. Diameter: About 7.3 mm. Internode length: About 4.7 cm. Texture and luster: Smooth, glabrous; matte. Strength: Strong. Color, developing: Close to N144C and 172A. Color, developed: Close to 146B. Thorns: Density: About one to two thorns per linear cm. Height: About 5.6 mm. Length, at base: About 1 cm. Color, immature: Close to 184A. Color, mature: Close to 164A and 199A.

Leaf description:

*Arrangement*.—Alternate; compound with typically five to seven leaflets per leaf.

*Leaf length*.—About 18.7 cm.

*Leaf width*.—About 6.2 cm.

*Leaflet length*.—About 13 cm.

*Leaflet width*.—About 4.9 cm.

*Leaflet shape*.—Ovate.

*Leaflet apex*.—Acuminate.

*Leaflet base*.—Obtuse.

*Leaflet margin*.—Serrate.

*Leaflet texture and luster, upper and lower surfaces*.—Smooth, glabrous; matte.

*Leaflet venation pattern*.—Pinnate.

*Leaflet color*.—Developing leaflets, upper surface: Close to 147A and 184A. Developing leaflets, lower surface: Close to 184B. Fully expanded leaflets, upper surface: Close to 138A; venation, close to 144D. Fully expanded leaflets, lower surface: Close to 138B to 138C; venation, close to 144D.

*Petioles*.—Length: About 1.6 cm. Diameter: About 2.1 mm. Strength: Moderately strong. Texture and luster, upper surface: Smooth, glabrous; semi-glossy. Texture and luster, lower surface: Smooth, glabrous; matte. Color, upper surface: Close to 143C. Color, lower surface: Close to 143C and 145D.

*Stipules*.—Arrangement and appearance: Two, adnate to the petiole, leafy in appearance. Length: About 3 cm. Width: About 2.3 mm. Shape: Roughly deltoid. Apex: Acuminate, tapered. Base: Tapered. Margin: Entire. Texture and luster, upper and lower surfaces: Smooth, margins, pubescent; membranous; matte. Venation pattern: Pinnate.

Flower description:

*Flower type and arrangement*.—Symmetrical rosette flowers; flowers typically grown as standard types with one terminal flower per flowering stem; flowers face upright.

*Flowering season*.—Plants of the new Rose flower year-round under greenhouse conditions; early flowering habit, plants begin flowering about four weeks after pinching.

*Flower diameter*.—About 12 cm.

*Flower depth* (*height*).—About 5.9 cm.

*Flower longevity*.—Excellent postproduction longevity; flowers maintain good substance for about 51 days on the plant and for about 20 days as a cut flower; flowers persistent.

*Fragrance*.—Moderately fragrant; pleasant.

*Flower buds*.—Length: About 6.3 cm. Diameter: About 4.7 cm. Shape: Ovoid. Texture and luster: Smooth, glabrous; semi-glossy. Color: Close to 143C and 178B.

*Petals*.—Quantity: About 24 to 27 per flower; petals imbricate. Length: About 6.7 cm. Width: About 6.9 cm. Shape: Nearly orbicular. Apex: Blunt to short acute. Base: Obtuse. Margin: Entire; moderately undulate. Texture and luster, upper and lower surfaces: Smooth, glabrous; matte. Color: When opening, upper surface: Close to 35B; towards the base, close to 54A. When opening, lower surface: Close to 26D. Fully opened, upper surface: Close to 43D; venation, close to 43D; color becoming closer to 162A, 67C and N167A with subsequent development. Fully opened, lower surface: Close to 52B; venation, close to 52B; color becoming closer to 162A, 67C and N167A with subsequent development.

*Petaloids*.—Quantity: About five to eight in a single whorl; size and shape are variable. Texture and luster, upper surface: Somewhat rugose, glabrous; matte. Texture and luster, lower surface: Smooth, glabrous; matte. Color: When opening, upper surface: Close to 37B to 37C. When opening, lower surface: Close to 27A. Fully opened, upper surface: Close to 52B; venation, close to 52B; color becoming closer to 167A with subsequent development. Fully opened, lower surface: Close to 38A; venation, close to 38A; color becoming closer to 167A with subsequent development.

*Sepals*.—Quantity per flower: Typically five in a single whorl. Length: About 5.2 cm. Width: About 1.8 cm. Shape: Roughly deltoid. Apex: Tapered. Base: Truncate. Margin: Entire; ciliate. Texture and luster, upper and lower surfaces: Pubescent, leathery; matte. Color: When opening, upper surface: Close to 143C and 178B. When opening, lower surface: Close to 147D. Fully opened, upper surface: Close to 143B. Fully opened, lower surface: Close to 147C to 147D.

*Reproductive organs*.—Stamens: Quantity: About 230 to 288 per flower. Filament length: About 7 mm. Filament color: Close to 3B and 58B. Anther size: About 4 mm by 1.9 mm. Anther shape: Reniform. Anther color: Close to 12A and 8C. Pollen amount: None observed. Pistils: Quantity: About 198 to 231 per flower. Pistil length: About 1.1 cm. Stigma diameter: About 1 mm. Stigma shape: Lobed. Stigma color: Close to 12A. Style length: About 7.4 mm. Style color: Close to 3D. Ovary color: Close to 2D. Receptacle height: About 1.8 cm. Receptacle diameter: About 1.4 cm. Receptacle shape: Cup-shaped. Receptacle texture: Smooth, glabrous. Receptacle color: Close to 144A. Fruits and seeds: To date, fruit and seed development have not been observed on plants of the new Rose.

Pathogen & pest tolerance: To date, plants of the new Rose have not been observed to be tolerant to pathogens and pests common to Rose plants.

Temperature tolerance: Plants of the new Rose have been observed to tolerate temperatures ranging from 9° C. to 23° C.

It is claimed:

1. A new and distinct Rose plant named 'ESM R432' as illustrated and described.

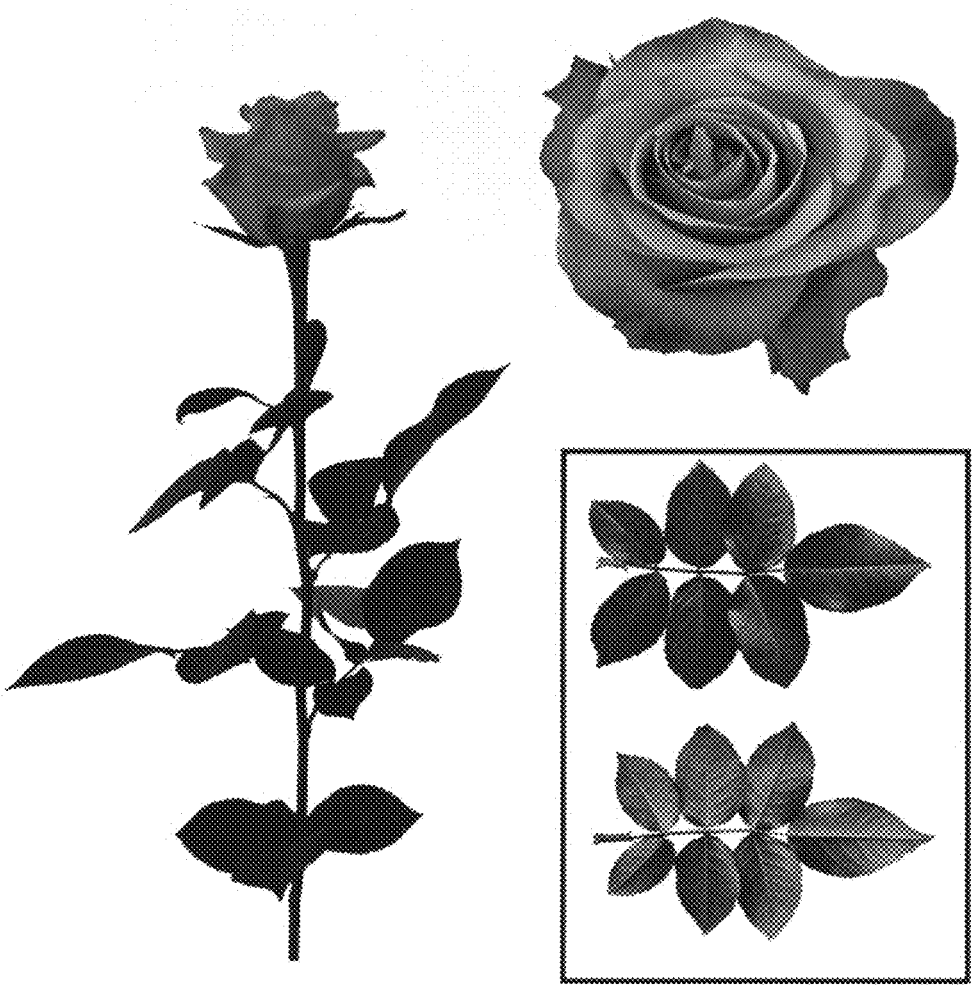

* * * * *